(12) United States Patent
Bahr et al.

(10) Patent No.: US 6,267,968 B1
(45) Date of Patent: Jul. 31, 2001

(54) MDP DERIVATIVES AND CONJUGATES HAVING HAEMATIPOIETIC FUNCTION STIMULATING ACTIVITY, AND COMPOSITIONS CONTAINING SAME

(75) Inventors: Georges Bahr, Puteaux; Pierre Lefrancier, Gif-sur Yvette; Louis Chedid, Paris, all of (FR)

(73) Assignee: Vacsyn S.A., Paris (FR)

( * ) Notice: Subject to any disclaimer, the term of this patent is extended or adjusted under 35 U.S.C. 154(b) by 0 days.

(21) Appl. No.: 09/302,145

(22) Filed: Apr. 29, 1999

Related U.S. Application Data (62) Division of application No. 08/930,862, filed on Oct. 7, 1997.

(30) Foreign Application Priority Data

Apr. 7, 1995 (FR) .................................................. 95 04194
Apr. 5, 1996 (WO) ...................................... PCTFR9600527

(51) Int. Cl.[7] .......................... A61K 37/02; C07C 103/52
(52) U.S. Cl. .............................. 424/279.1; 514/8; 514/19; 530/300
(58) Field of Search .......................... 424/279.1; 514/23, 514/13

(56) References Cited

U.S. PATENT DOCUMENTS 4,153,684 * 5/1979 Audibert et al. ....................... 424/88

FOREIGN PATENT DOCUMENTS

56992A1    8/1982  (EP) .
94/21275 * 9/1994  (WO) .

OTHER PUBLICATIONS

Database Caplus, DN 97: 125475. Wuest et al. Infect.Immunol. 37(2), 452–462, Feb. 1982.*
Namba et al. Blood, 83, 2480–2488, Apr. 1994.*
Namba et al Vaccine, 14(12) 1149–1153, Dec. 1996.*
Azuma et al. Vaccine, 10, 1000–1006, Aug. 1996.*
Database Caplus, DN 120:153073; Galicchio et al. Lithium, 4(3), 189–194, Mar. 1993.*
Physicians Desk Reference. http://www.pdrel.com.*
Krueger et al. J. Exp. Med. (1984), 159(1).68–76, Jan. 1984.*
Dinarello et al J. Infect. Disease, 138, 760–767, Jun. 1978.*
Chedid et al. Immunopathology, 7, 382–396, Mar. 1977.*

* cited by examiner

*Primary Examiner*—Michael Borin
(74) *Attorney, Agent, or Firm*—Birch, Stewart, Kolasch & Birch, LLP; Leonard R. Svensson

(57) ABSTRACT

Pharmaceutical compositions containing Muramyl dipeptide derivatives and conjugates or Muramyl dipeptide derivatives and conjugates combined with nucleoside derivatives which induce hematopoietic stem cell stimulation and mobilization into the circulating blood system. Methods to induce hematopoietic stem stimulation and mobilization, as well as methods to decrease myelotoxic effects using these pharmaceutical compositions.

13 Claims, 10 Drawing Sheets

FIG_1A

FIG_1B

FIG_2A

FIG_2B

FIG_3A

FIG_3B

FIG_6

FIG_7

MDP DERIVATIVES AND CONJUGATES HAVING HAEMATIPOIETIC FUNCTION STIMULATING ACTIVITY, AND COMPOSITIONS CONTAINING SAME

This application is a divisional of co-pending application Ser. No. 08/930,862, filed on Oct. 7, 1997. Application Ser. No. 08/930,862 is the national phase of PCT International Application No. PCT/FR96/00527 filed on Apr. 5, 1996 under 35 U.S.C. §317. The entire contents of each of the above-identified applications are hereby incorporated by reference.

BACKGROUND OF THE INVENTION

1. Field of the Invention

The invention relates to a pharmaceutical composition capable of stimulating the hematopoietic function so as to mobilize and give rise in the circulation to extremely high levels of stem cells originating from the bone marrow. This invention makes it possible to offer:

1) new antimyelotoxic therapies;
2) new methods for harvesting bone marrow stem cells, making it possible to replace marrow biopsies for the purpose of:
    a) autologous or homologous grafting,
    b) use in gene therapy techniques.

Said pharmaceutical composition comprises at least one MDP derivative of general formula (I) below, and an especially impressive example of which, for the subject of the invention, is Muradimetide of formula Nac—Mur—L—Ala—D—Glu—[OCH3]—OCH3 or MDPA dimethyl ester.

2. Description of the Related Art

Muramyl peptides and their ester derivatives are a family of molecules which have been described in numerous publications and numerous patents since the first description of N-Acetyl-Muramyl-L-Alanyl-D-isoGlutamine (MDP for muramyl dipeptide). Briefly, they are capable of exerting a wide variety of biological activities including an immunoadjuvant activity, an anti-infectious activity, an antitumor activity, an antiallergic activity and a regulation of cytokine secretion. However, a number of these muramyl peptides, while they can display most promising biological activities, often display side effects or drawbacks which prevent their use as a medicament, in particular toxic effects or a difficulty of formulation on account of their low solubility in aqueous solutions.

They display, in addition, a wide variability in their spectrum of action.

Very recently, it has been shown that the muramyl peptide diesters of general formula (I) below, and especially Muradimetide, possess the special property of being immunostimulatory, which has simultaneous advantages of efficacy, of formulation and of lack of toxicity, a plurality of advantages which had not been observed for other MDP derivatives; in particular, an immunomodulator which is active by external administration, in particular by oral administration by aerosol, can enable a wider and more flexible use of this immunostimulant to be envisaged; the advantage of good tolerability also occurs when this derivative is administered systemically.

The essential features of the properties already described for MDP derivatives are linked to a strengthening of the humoral or cellular immune system.

Surprisingly, the present invention is the outcome of the discovery according to which some types of MDP derivatives, represented below by the formulae (I), (II) and (III) in combination, where appropriate, with a compound of formula (IV) or the conjugates of formulae (V) and (VI), are capable of increasing the level of normal and immature formed elements of the blood, and especially of neutrophils in the circulating blood, in particular after administration of doses of AZT likely to decrease considerably the level of circulating leukocytes. In fact, after administration of the pharmaceutical composition, an increase in normal leukocytes is observed in the circulation, accompanied by a very large increase in myelocytes/promyelocytes, followed by an increase in the neutrophils and, later, in the lymphocytes. Most remarkably, this effect is observed very strongly even after a combined treatment involving highly myelotoxic doses of AZT.

All blood cells are derived from common stem cells whose origin is the bone marrow. Before reaching their final stage of differentiation, these cells pass through different steps: pluripotent stem cells can differentiate either into T or B prolymphocytes, or into stem cells of the erythrocytic, myelocytic, granulocytic and myelokaryocytic lines. In these different intermediate steps, they are not morphologically discernible and are designated by the terms promyelocyte/myelocyte for the youngest and metamyelocytes for those closest to differentiation.

In the text hereinafter, these undifferentiated cells will be designated collectively HSC for "hematopoietic stem cells".

In the normal state, the level of HSC is of the order of 1% of the white cells present in the blood.

It is advantageous to activate hematopoiesis and to mobilize HSC in the following three cases:

1) to counteract the myelotoxic effects of certain drugs in order to maintain a normal level of blood cells (especially of neutrophils),
2) to replace bone marrow biopsies by the harvesting of high levels of HSC in the circulating blood for the purpose of homologous or autologous grafting of marrow cells,
3) to obtain from the circulating blood a high level of HSC in order to use them as vectors for carrying out certain types of gene therapy.

1) Antimyelotoxic treatment.

Some treatments or medicaments give rise to myelotoxic effects, such as chemotherapies for cancer or for AIDS, immunotherapies or radiotherapies, leading to a dysfunction of the hematopoietic function and thereby dramatically increasing the risks of intercurrent infections. The pharmaceutical composition of the invention enables the decrease in the cells of the immune system resulting from this myelotoxicity, and especially in the neutrophils, to be counteracted.

In addition, some treatments which employ immunotherapy, in particular by cytokines, can also give rise to a cytotoxic effect for which the compositions of the invention can play the part of an antagonist.

2) Obtaining of cells enabling bone marrow grafting to be performed.

Anticancer treatments by severe chemotherapy or by radiotherapy give rise to a destruction of the cells of the blood and the cells of the immune system. In these cases, the hematopoietic system is reconstituted by grafting bone marrow cells. Autologous grafts are performed when the cancer affects cells other than those of the marrow and, in this case, samples are taken from the patient himself before the destructive treatment. Homologous grafting (that is to say using cells originating from a compatible donor) is performed when the marrow cells are themselves cancerous.

In both cases, it is extremely advantageous to be able to enrich the bone marrow with stem cells, but most particularly to be able to obtain the latter in the circulating blood in a sufficiently high number to facilitate their use as grafts. In fact, at the present time, the use of blood for the preparation of grafts enriched with HSC requires the taking of a large number of large samples, which is hence spread out over a long period; furthermore, it is necessary to implement a preparation which is distressing for the patient and for the donor, since enrichment with HSC is carried out by administration of expensive and sometimes poorly tolerated cytokines (GM-CSF), followed by the taking of a large number of large blood samples, the collective treatments necessitating hospitalization every time. The pharmaceutical composition of the invention enables the material needed for marrow grafting to be obtained in ambulatory subjects and after only a few days of treatment, since it is capable of inducing in the blood, after approximately 4 days of treatment, a multiplication of the number of HSC by 200.

3) Obtaining of readily purifiable stem cells which can be used for gene therapy.

The use of certain forms of gene therapy techniques will depend on the possibility of obtaining HSC in large amounts in the circulating blood. This objective can be achieved by means of the pharmaceutical composition of the invention, enabling an extremely large percentage of HSC to be obtained in the blood, whereas these cells are very difficult to purify from the bone marrow.

Preclinical experiments and clinical trials of gene therapy showed that it was necessary to use stem cells which have a long life and a high power of expression and which distribute themselves throughout the body. It is very generally accepted that HSC are especially advantageous gene vectors, either for counteracting immune deficiencies such as Gaucher's disease or cases of profound immune deficiencies (SCID for severe combined immune deficiencies), or for counteracting the development of cancers such as myeloma, leukemia, cancer of the breast or ovary, and the like, or for inducing a resistance to infectious diseases, especially AIDS.

To meet these objectives, it is hence essential to have at one's disposal a large number of HSC which can be readily purified from the circulating blood by the usual cell separation techniques, and this is precisely the situation afforded by the composition of the invention or the medicaments containing it.

The composition of the invention makes it possible to envisage the development of the use of the cells of the circulating blood to reconstitute the hematopoietic function after cellular destruction, as a result of a multiplication, which can reach a factor of 200, of the percentage of circulating HSC, whereas, in the absence of treatment, not more than 1% of these cells can be detected.

This effect on the HSC occurs irrespective of the stage of differentiation of said stem cells, as shown in Example 7 below.

BRIEF SUMMARY OF THE INVENTION

The present invention, which is the outcome of this discovery of the novel properties of certain MDP derivatives, relates to a new pharmaceutical composition intended for preventing or treating the myelotoxic effect of certain treatments or diseases and/or stimulating the hematopoietic function, characterized in that it contains as active principle at least one compound of the following formula (I):

with
  R=H or $CH_3$
  X=L—Ala or L—Thr
  Rα=$NH_2$ or $O(CH_2)_xH$ with x=1 to 4
  Rγ=OH (except if Ra=NH2) or
  $O(CH_2)_xH$ with x=1 to 4
or muroctasine of the following formula (II): NaC—Mur—L.Ala—D—isoGln—N°—stearoyl—L—Lys.

or MTP—PE of the following formula (III): monosodium Nac—Mur—L—Ala—D—isoGln—L—alanyl-2-(1', 2'-di-palmitoyl-sn-glycero-3'-phosphoryl)ethylamide An especially impressive example of compound corresponding to the formula (I) is Muradimetide of formula:

Nac—Mur—L—Ala—D—Glu[OMe]—OMe.

This composition enables a normal or above normal level of the formed elements of the blood, in particular the erythrocytes and the platelets, to be restored.

BRIEF DESCRIPTION OF THE DRAWINGS

FIG. 1 shows the effect of an oral treatment of mice with Muradimetide in combination with nonmyelotoxic (5 mg per kg) (FIG. 1A) or myelotoxic (40 mg per kg) (FIG. 1B) doses of AZT on the change in circulating leukocytes.

FIG. 2 depicts the same type of diagram for the neutrophil count.

FIG. 3 represents the same type of diagram for the myelocyte count.

DETAILED DESCRIPTION OF THE PREFERRED EMBODIMENTS

The desired effect of these compounds is obtained in a composition in which the dosage of the compounds of formula (I), (II) or (III) is such as to permit an oral administration at doses of 0.1 to 25 mg per kg body weight in man or animals, or a systemic administration in which the active principle is dosed in such a way as to permit an administration of 0.05 to 2.5 mg per kg body weight and per dose.

Treatment with AZT has the drawback of myelotoxicity. Surprisingly, the joint administration of a derivative of formula (I) or (II) or (III) with a nucleoside derivative of general formula (IV) below leads to an increase by a factor of 10 to 300, and often around 200, in the HSC level in the blood, and the compositions of the invention advantageously contain, besides a derivative of formula (I), (II) or (III), a derivative of formula (IV).

(IV)

B being a purine or pyrimidine base
R=H, N₃ or a halogen.

An example of this derivative is 3'-azido-3'-deoxythymidine (AZT). Combination can also take place with all nucleosides displaying myelotoxic and antiretroviral activities similar to that of AZT, and in particular nucleosides containing ribose and not deoxyribose. Wherever we mention AZT hereinafter in the description, a person skilled in the art will know that, in similar uses, other nucleosides may be used and be considered to be equivalents of AZT.

When AZT is combined with the MDP derivative in a composition of the invention, the latter contains an amount thereof enabling it to be administered as a dose of between 1 and 150 mg/kg orally or systemically, it being possible for this daily dose to be administered in a single portion or several portions.

The simultaneous administration of MDP derivatives of formula (I), (II) or (III) with a derivative of formula (IV) may be carried out:

- either within a medicament containing at least these two compounds, such a medicament forming part of the invention,
- or by the simultaneous administration of two medicaments, each of which contains one type of compound, simultaneous administration meaning that the compounds can exert their effects during at least a period of overlap,
- or by the production of conjugates combining the compounds of formula (I) and (IV) in the same molecule.

Simultaneous administration should naturally be understood to mean that the administration may be carried out in the same formulation systemically or orally or, on the contrary, in two different formulations and administered within a sufficiently small time interval for the effects of one or other active principle to be experienced simultaneously.

The invention also relates to conjugates displaying an antimyelotoxic effect or enabling the hematopoietic stem cells to be mobilized in the circulating blood, characterized by one of the following formulae:

(V)

with
R=H or CH₃
Rα=NH₂ or O(CH₂)ₓH with x=1 to 4

X=L—Ala or L—Thr
x=0, 1 or 2
Y=an amino acid residue
with A being a nucleoside containing, at the 5' position of the deoxyribose residue, either a hydroxyl function or an amine function, and at the 3' position a hydrogen, a halogen or an azide group.

An advantageous conjugate corresponding to the formula (V) is the one in which:
R=CH₃
X=L—Ala
x=1
Y=L—Ala
Rα=OCH₃

Another conjugate of the invention corresponds to the formula:

(VI)

in which
X=L—Ala or L—Thr
Y is an arm, such as a dicarboxylic acid, in particular a succinyl residue,
Z=O or NH,
R=H or CH₃,
Rα and Rγ have the meaning given in the formula (I), with A being a nucleoside containing, at the 5' position of the deoxyribose residue, either a hydroxyl function or an amine function, and at the 3' position a hydrogen, a halogen or an azide group.

An advantageous conjugate corresponding to the formula (VI) is the one in which:
X=L—Ala
R=CH₃
Rα=OCH₃ and Rγ=OCH₃
Y=CO—(CH₂)₂—CO
Z=O
A is AZT.

The present invention also relates to pharmaceutical compositions which can be used as antagonists of the myelotoxic effects of certain treatments or medicaments, characterized in that it contains as active principle a conjugate of formula V or VI in combination with a vehicle which is pharmaceutically acceptable for an oral administration or for a systemic administration.

These compounds are new and the methods for synthesizing them form part of the invention.

To synthesize the compounds of formula (V), the amine or hydroxyl functions possibly present in the purine or pyrimidine base residue of a 2'-deoxyribonucleoside are temporarily masked by groups affording temporary protection; the function at the 5' position of the nucleoside derivative can be optionally converted to an amine function via a mesyl group which can be modified to an azide which can be finally hydrogenated to an amine function; the function at the 3' position of the nucleoside derivative can be either a hydrogen, a halogen or an azide group, or a mesyl group which can be subsequently replaced by nucleophiles such as azide or halogen.

The hydroxyl or amine function at the 5' position of the nucleoside derivative is coupled, in particular by a mixed anhydride method or alternatively a carbodiimide method, optionally using certain additives such as imidazole, hydroxybenzotriazole or alternatively DMAP (dimethylaminopyridine), to a muramyl peptide derivative of formula (I) in which Rγ is a hydroxyl or an amino acid residue.

If Rγ is an amino acid residue, it is possible to effect the coupling of the nucleoside derivative with the protected amino acid first, and then the coupling after deprotection to a muramyl peptide derivative of formula (I) in which the γ-carboxyl function of the glutamyl residue is free.

At the end of the process, to obtain the conjugates of type (V), the temporary protective groups which can be present are removed and, where appropriate, the mesyl group at the 3' position is converted to an azide or a halogen.

A variant consists in coupling (i) the hydroxyl or amine function at the 5' position of the nucleoside derivative with a protected amino acid, and then, in successive steps, according to techniques used in peptide synthesis, (ii) a suitably protected D-glutamic acid derivative, (iii) a protected L-alanine or L-threonine derivative, and (iv) a protected N-acetylmuramic acid derivative. At the end of the procedure, to obtain the conjugates of type (V), the temporary protective groups are finally removed and, where appropriate, the mesyl group at the 3' position is converted to an azide or to a halogen.

The synthesize a compound of formula (VI), the amine or hydroxyl functions possibly present in the purine or pyrimidine base residue of a 2'-deoxyribonucleoside are temporarily masked by groups affording temporary protection; the function at the 5' position of the nucleoside derivative can be optionally converted to an amine function via a mesyl group which can be modified to an azide which can be finally hydrogenated to an amine function.

The function at the 3' position of the nucleoside derivative can be either a hydrogen, a halogen or an azide group, or a mesyl group which can be subsequently replaced by nucleophiles such as azide or halogen.

The hydroxyl or amine function at the 5' position of the nucleoside derivative is coupled, in particular by a mixed anhydride method or alternatively a carbodiimide method, optionally using certain additives such as imidazole, hydroxybenzotriazole or alternatively DMAP, to a muramyl peptide derivative of formula (VI) in which, A being nonexistent:

the anomeric hydroxyl (C1) is or is not temporarily protected,

Z is NH or O,

Y is a dicarboxylic acid residue, in particular a succinyl residue.

Such muramyl peptide derivatives are prepared from muramyl peptide derivatives of formula (I), the method of synthesis of which is now well known, with the anomeric hydroxyl (C1) temporarily protected by a benzyl glycoside which is susceptible to hydrogenolysis or any other appropriate group, and the hydroxyls at the 4 and 5 positions protected by benzylidene groups which are susceptible to hydrogenolysis or isopropylidene groups which are susceptible to acidolysis. The removal of this temporary protection makes it possible either to liberate the primary hydroxyl function (C6) and to substitute it with a succinyl group, for example, or to convert it to an amine function via a mesyl group which can be modified to azide which can be finally hydrogenated to an amine function. This amine function is then substituted with a succinyl group, for example.

At the end of the process, to yield the conjugates of type (VI), the temporary protective groups which can be present are removed and, where appropriate, the mesyl group at the 3' position is converted to an azide or a halogen.

The present invention also relates to the use of a compound of formula (I), (II), (III), (V) or (VI) in the manufacture of a medicament which is an antagonist of the myelotoxic effects of certain treatments or medicaments, or enabling the hematopoietic function to be stimulated in the general circulation, alone or in combination with a compound of formula (IV).

Such a use is especially recommended for counteracting the myelotoxic effects of certain chemotherapies for treating AIDS or certain cancers.

The term combination is understood to mean that the two compounds are administered either in the same pharmaceutical composition or in a different composition, the two compositions then being administered to man or to animals within a time interval such that at least a part of the effects of each component occur simultaneously.

Such a use enables the medicament in question to enrich the circulating blood in hematopoietic stem cells; this enrichment is especially advantageous either when it is desired to perform bone marrow grafting, either of autografts or of allografts, or alternatively for using HSC to perform gene therapies, since, as has been explained above, the totipotent cells constituted by the HSC are the best candidates for a good expression of a heterologous gene after reinjection into the patient systemically. It is then necessary to have very high concentrations of HSC in the blood at one's disposal at a given time; it is then expedient to give during a short time interval doses of AZT which are higher than the usual doses recommended for repeated administrations over long periods; it should be noted, in addition, that the doses of AZT administered are similar and lie within the same ranges irrespective of whether the administration is parenteral, oral or systemic.

This use is characterized in that the compound of formula (I) is Muradimetide of formula, Nac—Mur—L—Ala—D—Glu[OMe]—OMe, or in that the derivative of formula (II) is muroctasine or in that the derivative of formula (III) is MTP—PE.

The compound of formula (IV) is 3'-azido-3'-deoxythymidine (AZT) in a preferred use of the invention.

Lastly, the invention covers the methods of treatment with the compositions of the invention in order to offset the myelotoxic effects of certain chemotherapies, or alternatively to increase the concentration of HSC in the blood.

The examples which follow, given without implied limitation, are designed to show the altogether surprising effect of one of the compounds of the family in their new use. They are performed in mice, and illustrated by Tables 1, 2 and 3 which are placed in the text, and by FIGS. 1 to 13, the meaning of which is described below, illustrate unambiguously the particular effect of one of the components of the class covered by the formula (I), namely Muradimetide, both on the antimyelotoxic effect and on the mobilization of HSC in the blood circulation, this effect not occurring with other MDP derivatives such as MDPA or with lymphokines customarily used to stimulate myelocytes, such as GM—CSF.

EXAMPLE 1

Activity of Muradimetide Administered Alone

Table 1 below depicts the leukocyte, neutrophil, lymphocyte and myelocyte counts as a function of the time after treatment with Muradimetide alone administered at a dose of 25 mg/kg. The treatment is performed for 4 consecutive days by intravenous injection.

TABLE 1

Effect of 4 consecutive days of intravenous treatment of mice with Muradimetide (25 mg/kg) on the modifications of the number of normal circulating leukocytes (predominantly neutrophils and lymphocytes) and immature circulating leukocytes (myelocytes).

| Day of measurement | No. of Leukocytes ($\times 10^5$/ml) | No. of Neutrophils ($\times 10^5$/ml) | No. of Lymphocytes ($\times 10^5$/ml) | No. of Myelocytes ($\times 10^4$/ml) |
|---|---|---|---|---|
| 0 | 50 ± 14° | 11 ± 3 | 38 ± 12 | 7 ± 6 |
| 2 | 52 ± 12 | 10 ± 3 | 41 ± 17 | 8 ± 8 |
| 3 | 52 ± 17 | 13 ± 5 | 35 ± 13 | 40 ± 5* |
| 4 | 52 ± 15 | 12 ± 4 | 34 ± 8 | 72 ± 27* |
| 7 | 50 ± 13 | 12 ± 4 | 38 ± 10 | 4 ± 4 |

°Mean ± standard deviation (3 mice per group).
*Significantly higher than the values on day 0.

This table shows clearly that Muradimetide administered alone induces on days 3 and 4 an increase in the number of circulating myelocytes which is highly significant.

EXAMPLE 2

Effect of a treatment with Muradimetide on the increase in the number of neutrophils, leukocytes and myelocytes after a treatment with AZT.

Treatment with AZT alone classically induces a decrease in the number of circulating leukocytes and neutrophils. This decrease is followed by a restoration occurring approximately 4 to 7 days after the beginning of the treatment. When Muradimetide has been administered systemically or orally after a treatment with 40 mg/kg of AZT, there is no fall in the number of cells and, on the contrary, there is a multiplication by at least 1.5 of the number of leukocytes and a tripling of the number of neutrophils, this already occurring after 4 days. The results are depicted in Table 2 below.

Male CDI mice (5 per group) were injected with AZT at a dose of 40 mg per kg on days 0 to 3. Muradimetide is administered on the same days at a dose of 10 mg per kg intravenously or 50 mg per kg orally. Cell counts are done an day 0 (before the treatment) and on days 3 and 4.

TABLE 2

Effect of the intravenous or oral treatment of mice with Muradimetide on the modifications of the cell counts induced by intravenous administration of AZT (40 mg/kg):

| Treatment (days 0–3) | Day of measurement | Leukocytes ($\times 10^6$/ml) | Neutrophils ($\times 10^6$/ml) | Myelocytes ($\times 10^4$/ml) |
|---|---|---|---|---|
| physiological saline | 0 | 5.9 ± 1.5* | 1.5 ± 0.4 | 14 ± 8 |
| Muradimetide i.v.; (10 mg/kg) | | 6.0 ± 3.4 (NS)° | 2.0 ± 1.3 (NS) | 5 ± 7 (NS) |
| Muradimetide p.o (50 mg/Kg) | | 4.8 ± 0.4 (NS) | 1.4 ± 0.5 (NS) | 14 ± 13 (NS) |
| physiological saline | 3 | 4.2 ± 0.5* | 1.0 ± 0.2 | 2 ± 4 |
| Muradimetide i.v.; (10 mg/kg) | | 5.9 ± 2.9 (NS)° | 1.5 ± 0.8 (NS) | 145 ± 83 (0.0143)) |
| Muradimetide p.o (50 mg/Kg) | | 6.1 ± 1.4 (NS) | 1.6 ± 0.5 (NS) | 123 ± 55 (0.0090)) |
| physiological saline | 4 | 5.3 ± 1.0* | 1.3 ± 0.5 | 33 ± 14 |
| Muradimetide i.v.; (10 mg/kg) | | 7.6 ± 1.6 (0.0143)° | 4.6 ± 1.5 (0.0143)) | 117 ± 46 (NS) |
| Muradimetide p.o (50 mg/Kg) | | 8.1 ± 2.9 (NS) | 4.3 ± 2.47 (0.0472) | 138 ± 59 (0.0090) |

*Mean±standard deviation (5 mice per group).
°Not significantly different from the group treated with physiological saline Table 2 shows the spectacular increase in the percentage of myelocytes or of promyelocytes in the presence of Muradimetide irrespective of its mode of administration.

EXAMPLE 3

Effect of combined oral treatment with AZT and Muradimetide on the red cells and the platelets.

Figure 9:
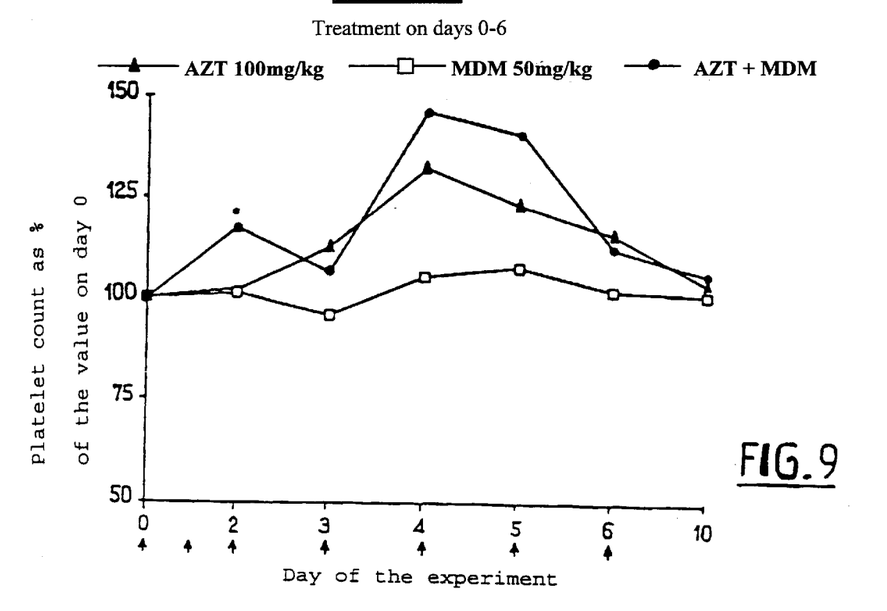
FIG. 9 represents the effect of the oral treatment of BALB/c mice for 7 consecutive days with AZT, Muradimetide (MDM) or a mixture of these compounds on the platelet count.
Figure 10:
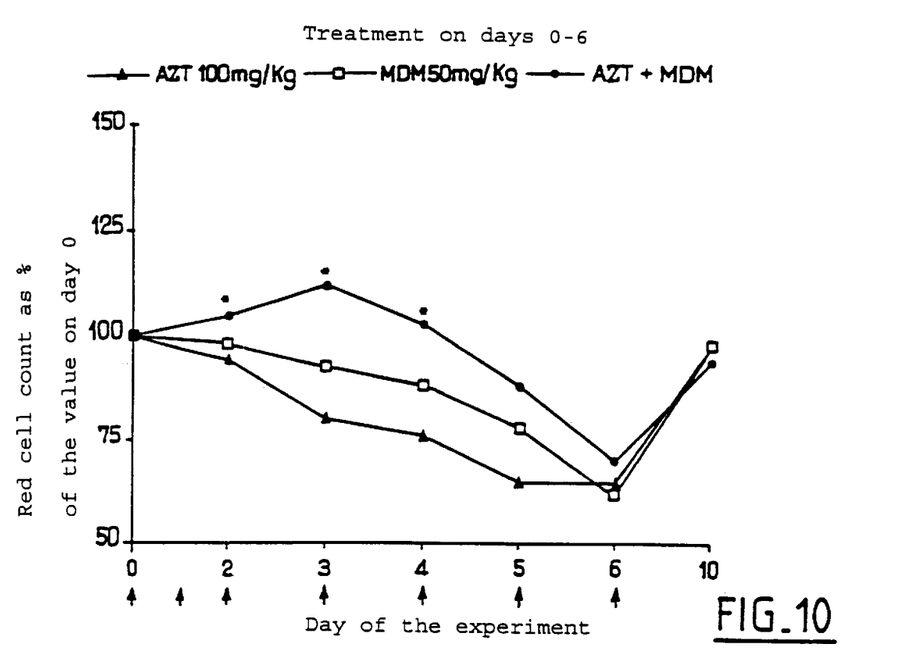
FIG. 10 represents the effect of the oral treatment of BALB/c mice for 7 consecutive days with AZT, Muradimetide or a mixture of these compounds on the number of red cells.

The effect of a 7-day treatment on the number of red cells and of platelets is seen in FIGS. 9 and 10, respectively. The counts are shown as a percentage of those obtained on day 0. Female BALB/c mice (5 per group) are treated once daily for 7 consecutive days with 100 mg/kg of AZT (Δ), 50 mg/kg of muradimetide (□) or simultaneously with 100 mg/kg of AZT and 50 mg/kg of muradimetide (○). Platelet or red cell counts were done on day 0 and up to 10 days following the beginning of the treatment. No toxicity on the platelets is seen, either with AZT, muradimetide or the mixture of these compounds. The upward trend in their number is apparent between days 4 and 5. On the other hand, the anemia which could be observed in the treated groups could be due to the repeated bleedings; nevertheless, the rate and extent of the anemia is greatly reduced in the animals treated with the mixture of the two products, in comparison with that observed in the group treated with AZT alone. This suggests a potential effect of the mixture to offset the toxicity of AZT not only on the leukocytes but also on the red cells.

EXAMPLE 4

Mobilization of HSC after a combined oral treatment with AZT and Muradimetide.

Figure 11:
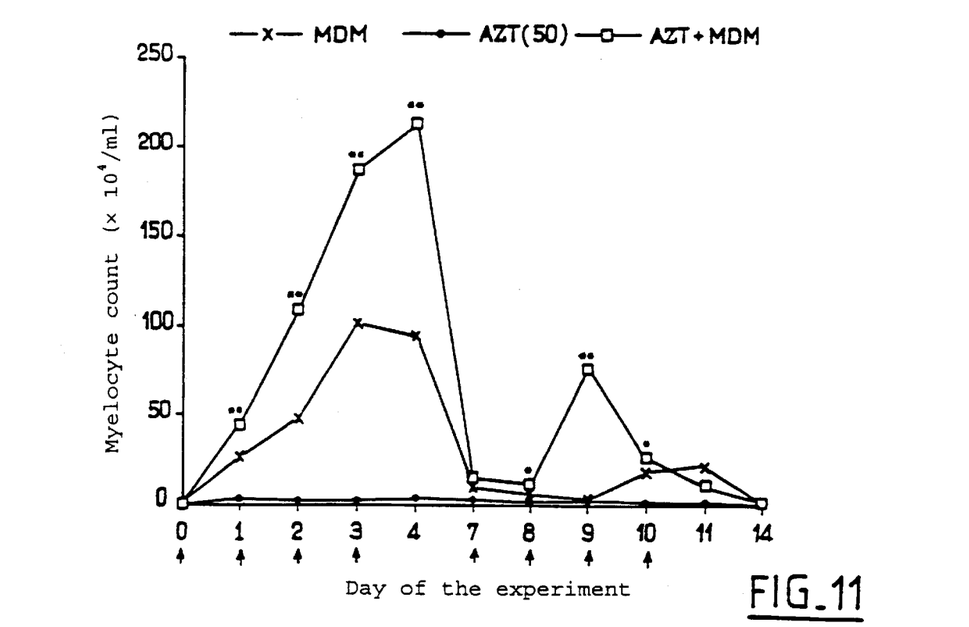
FIG. 11 represents the effect of an oral treatment of mice for two consecutive weeks (4 days per week) with AZT, Muradimetide or the mixture of the two on the number of circulating myelocytes.

Table 3 below and FIG. 11 show the effect of an oral treatment of mice with Muradimetide before, at the same time as or after AZT administered at 50 mg per kg, on the number of circulating myelocytes tested 24 hours after 4 daily administrations.

TABLE 3

| Time of p.o. treatment with | | | | |
|---|---|---|---|---|
| AZT (50 mg/Kg) | Muradimetide (25 mg/Kg) | n = | No. of circulating myelocytes (× $10^4$/ml) | P-Value |
| 0 h | — | | 6 ± 8$^\Delta$ | — |
| — | 0 h | 5 | 17 ± 15 | NS |
| 0 h | 0 h | 5 | 215 ± 51 | 0.0090 |
| 0 h | −4 h | 5 | 194 ± 50 | 0.0090 |
| −4 h | 0 h | 5 | 187 ± 42 | 0.0090 |

The mean number of circulating myelocytes before the treatment lies between 3 and 15×10$^4$ cells per ml in the 5 groups.

The "P-value" was calculated by the Mann Whitney U Rank test.

NS means that the difference is not significant. This table confirms that the increase in circulating myelocytes is approximately 200 when there is a joint effect of AZT and Muradimetide. The two constituents of the combination were administered orally either simultaneously or at separate times.

FIG. 11 shows the effect of a treatment with MDM at 25 mg/kg (X), of AZT at 50 mg/kg (○) and of the mixture of the two (□) on the myelocyte count of mice treated for 2 weeks on days 0, 1, 2 and 3 of the first week and 7, 8, 9 and 10 of the second week. It is clearly apparent that muradimetide alone, and most particularly the mixture of muradimetide and AZT, have a significant effect on the mobilization of HSC whereas AZT alone plainly has no effect. That the effect is most particularly pronounced in the first week shows that the treatment necessitates a certain lapse of time between the different treatment cycles, and that repeated treatments could, where appropriate, be useful.

EXAMPLE 5

Effect of an oral treatment of AZT, of MDM and of a mixture of these compounds on the circulating myelocyte count of splenectomized mice.

Figure 12:
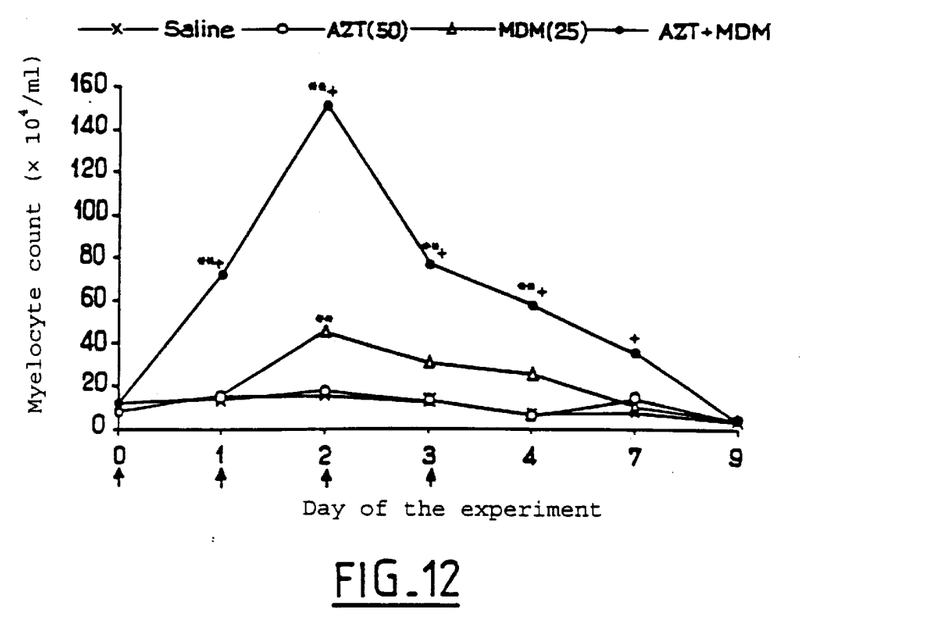
FIG. 12 represents the same experiment as represented in FIG. 11, on mice which have undergone an ablation of the spleen.

It is known in the mouse that, in addition to the marrow, the only organ having hematopoietic activity is the spleen. Thus, in order to determine whether the effect of the MDM+AZT mixture on the mobilization of HSC originates from the spleen or from the marrow, AZT at 50 mg/kg (○), MDM at 25 mg/kg (Δ) and the mixture of these compounds (○) were administered to mice which had been splenectomized 10 days beforehand. The results obtained are depicted in FIG. 12, where it is obvious that administration of the mixture for 4 successive days leads to a very marked appearance of circulating myelocytes in the peripheral circulation, this occurring with an intensity similar to that observed in normal mice (FIG. 11), and the increase in HSC is already apparent at the second injection. This clearly implies that this mobilization of HSC originates from the marrow and not from the spleen, which is extremely important for extrapolating such a treatment to man, in whom the bone marrow is the tissue which is very predominantly responsible for the hematopoietic function.

EXAMPLE 6

Effect of the oral administration of AZT, MDM or the mixture of these compounds on the mobilization of HSC of cyclophosphamide-treated mice.

The effect of the above treatment in offsetting the cytotoxic effect of chemotherapies was studied by treating mice with cyclophosphamide.

Figure 13:
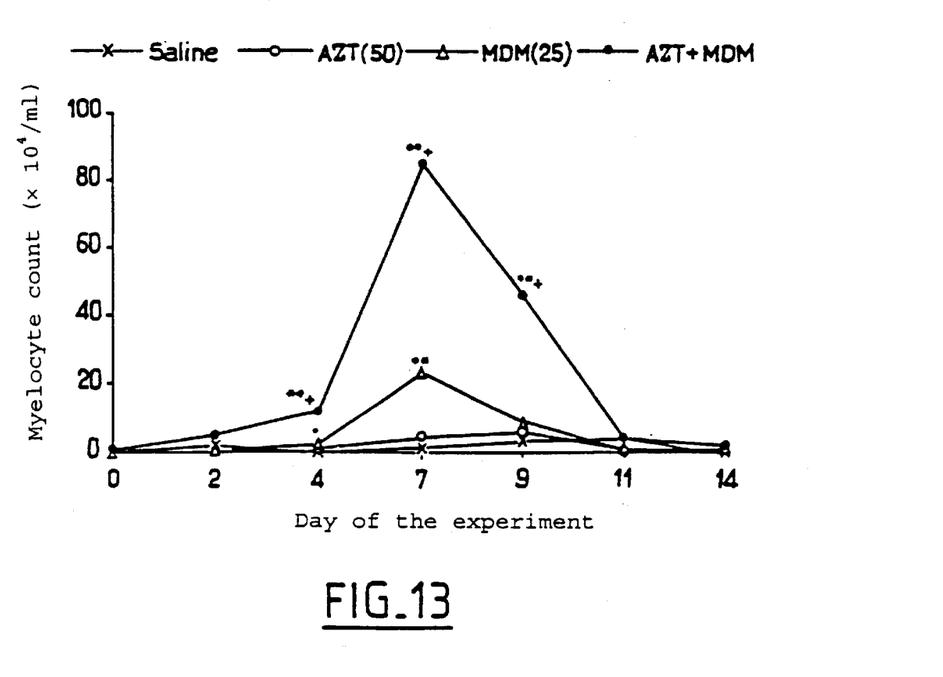
FIG. 13 represents a similar experiment on normal mice which have previously received a treatment with a cytotoxic drug: cyclophosphamide.

The mice, treated with a single subcutaneous injection of cyclophosphamide (dose of 200 mg/kg) on day 0, were then divided into 4 groups and received orally, besides physiological saline (X), AZT at 50 mg/kg (□), MDM at 25 mg/kg (Δ) or mixture of these compounds (○). The oral treatment was performed on days 0, 1, 2 and 3 and the cell counts were evaluated up to 14 days after the beginning of the treatment. The results are shown in FIG. 13. Here too, it is seen to be obvious that a very strong mobilization takes place, most particularly in the presence of the mixture of AZT and MDM. A similar but markedly less pronounced effect of MDM administered alone was also observed on the circulating neutrophil count.

EXAMPLE 7

Effect of the compositions of the invention on the mobilization of HSC according to their different stages of differentiation.

The objective of these experiments is to demonstrate the different HSC populations present in the circulating blood.

The following stages were looked for, from the most primitive ones discernible in culture and which do not display any sign of differentiation, such as the CAFC (coblestone area forming cells) and LTC-IC (long term culture-initiating cells), to the GM-CFU (granulocyte macrophage-colony forming units) passing through intermediate stages such as the HPP and LPP-CFU (high proliferating potential and low proliferating potential CFU, respectively). In all cases, the culture conditions, especially their duration, were chosen to permit an optimal detection of the different populations in question.

Figure 14A:
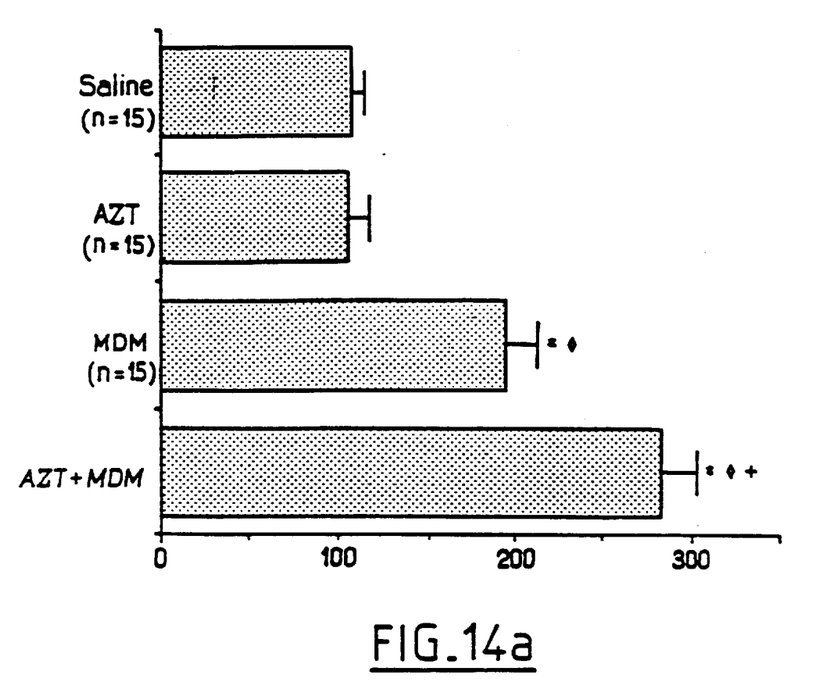
FIG. 14a is a graph illustrating the number of granulocyte-macrophage colony forming units (GM-CFU) in the circulating blood of mice after injection with saline, AZT, muradimetide (MDM) or AZT muradimetide.
Figure 14B:
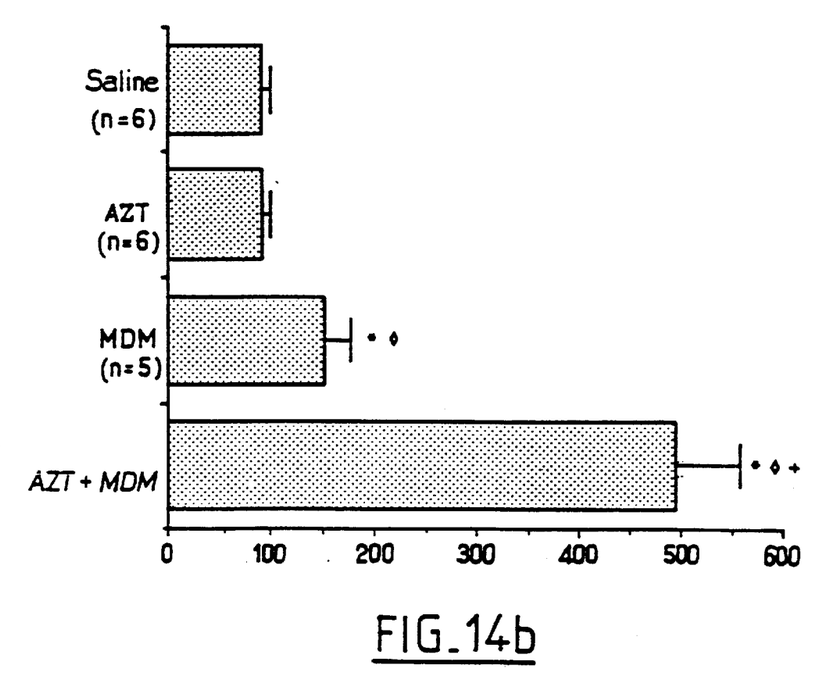
FIG. 14b is a graph illustrating the number of low proliferation potential (LPP) colony forming units in the circulating blood of mice after injection with saline, AZT, muradimetide (MDM) or AZT and muradimetide.
Figure 14C:
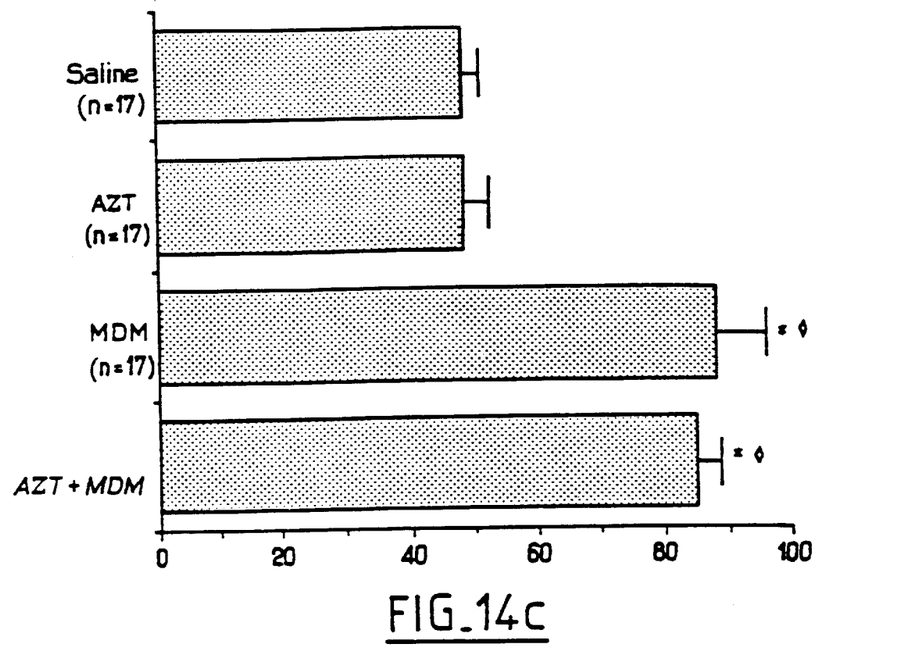
FIG. 14c is a graph illustrating the number of high proliferation potential (HPP) colony forming units in the circulating blood of mice after injection with saline, AZT, muradimetide (MDM) or AZT and muradimetide.
Figure 14D:
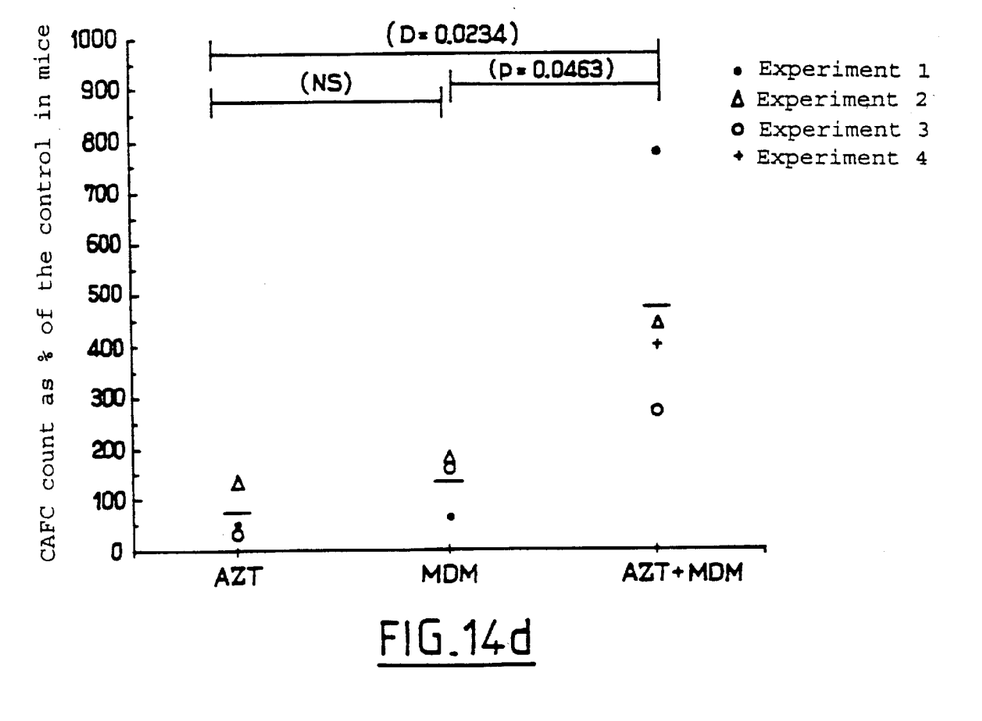
FIG. 14d is a graph illustrating the coblestone area forming cells (CAFC) count as the percentage of control in the circulating blood of mice after injection with saline, AZT, muradimetide (MDM) or AZT and muradimetide.

For this study, the effect of injecting saline (X—), AZT at 50 mg/kg, MDM at 25 mg/kg and the mixture of the two on the number of circulating HSC were compared. The mononuclear cells after purification were cultured for 5 days in order to count the GM-CFU (for granulocyte-macrophage colony forming units), for 28 days to count the low proliferating potential (LPP) colony forming units and the high proliferating potential (HPP) CFU. The CAFC were counted after 14 days of culture. The LTC-IC after 28 days. The results are presented in FIGS. 14a, 14b, 14c and 14d, respectively. The mice (10 Balb/c per group) received once daily and for three consecutive days either physiological saline, or AZT, or MDM or the mixture of the two under the above dose conditions. Twenty-four hours after the last administration, the blood of all the mice in each group was collected. For the experiments depicted in FIGS. 14a, 14b and 14c, the mononuclear cells were then separated on density gradients and cultured in a semisolid medium for a period of 5 days for the GM-CFU and 28 days for the LPP-CFU. In all these diagrams, the effect of MDM alone, and most particularly of the mixture of MDM and AZT, is clearly apparent.

To measure the effect of the treatment on the CAFC and the LTC-IC, the blood was collected 24 hours after the last administration of product, and the mononuclear cells were then purified and cultured at different cell densities on a nutrient layer of irradiated cells. The count was done 14 days after setting up the cultures and is presented as a percentage of number of cells obtained in the control cells treated with physiological saline. The figures give the mean of 3 or 4 independent experiments. When culturing is continued for 28 days, LTC-IC (for long term culture initiating cells) cells form, and the effect of the treatments on the formation of these cells after 28 days of treatment is similar to that observed in the case of CAFC.

All these experiments show the especially efficient effect of the simultaneous oral treatment of AZT and MDM on the mobilization of HSC at all the stages of differentiation.

EXAMPLE 8

Effect of an oral treatment of mice with Muradimetide in combination with nonmyelotoxic or myelotoxic doses of AZT on the changes in the circulating leukocyte and neutrophil counts.

Figure 1A:
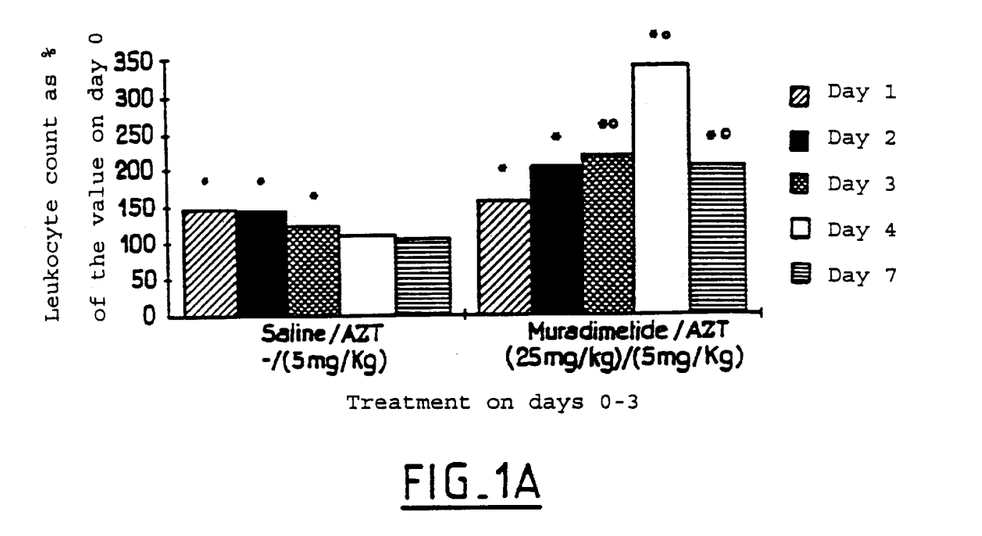
Figure 1B:
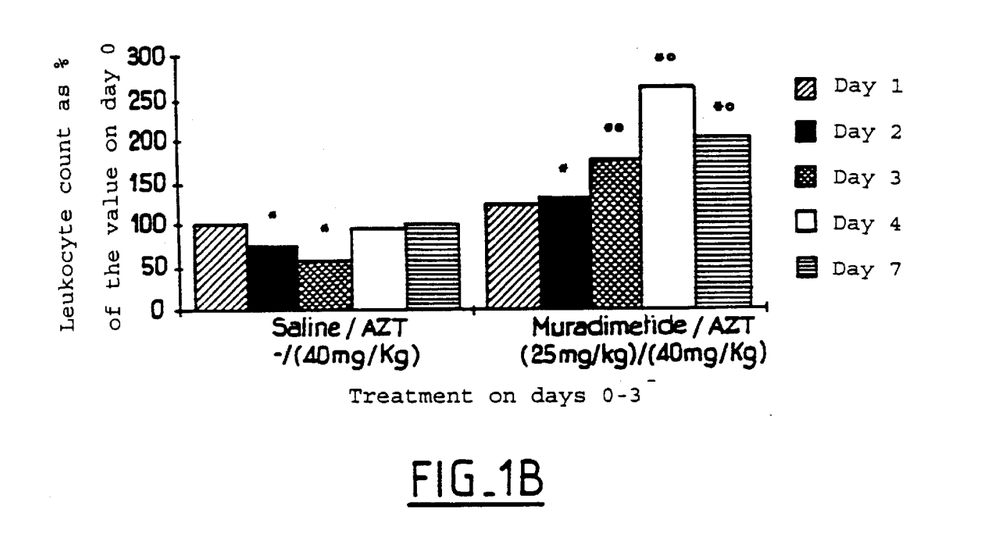
Figure 2A:
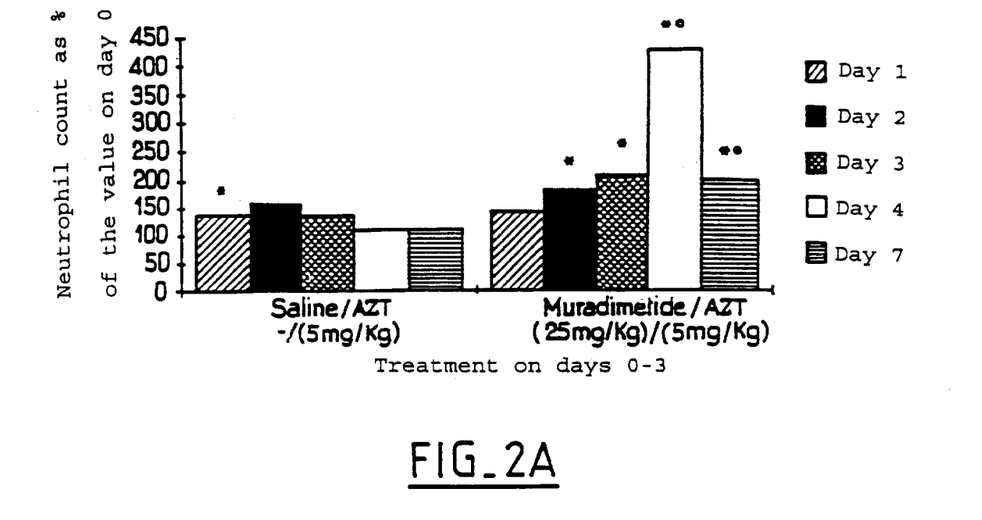
FIG. 2A represents an experiment carried out with nonmyelotoxic dose of AZT (5 mg per kg) and FIG. 2B with myelotoxic dose of AZT (40 mg per kg).
Figure 2B:
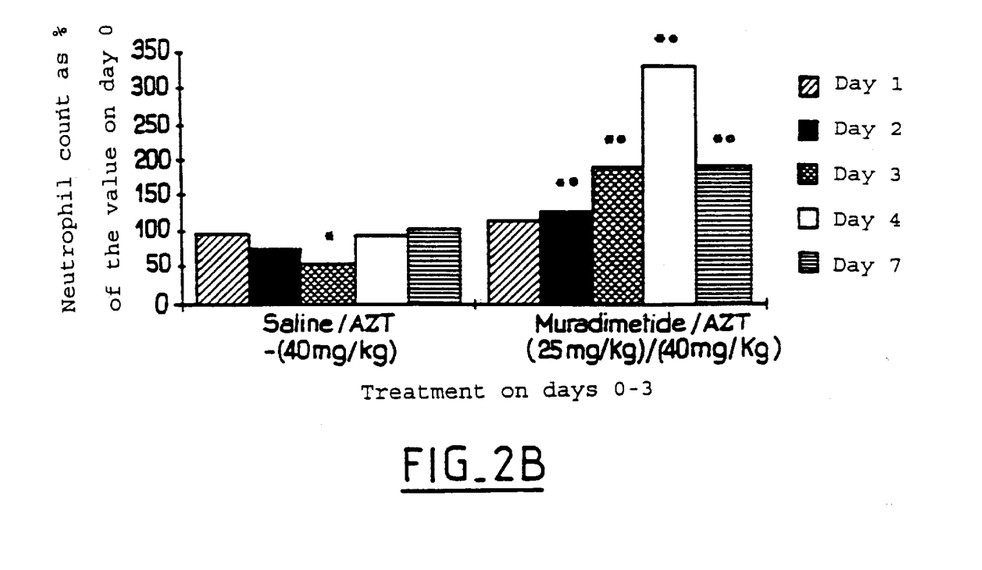

This effect is shown in FIGS. 1 and 2, FIGS. 1A and 2A representing a nonmyelotoxic dose of AZT and FIGS. 1B and 2B representing a myelotoxic dose of AZT.

In this experiment female Swiss mice were injected intravenously with AZT at a dose of 5 or 40 mg per kg on days 0, 1, 2 and 3. On each of the 4 days, and 4 hours before the administration of AZT, groups of mice consisting of 5 individuals received orally either buffer or Muradimetide at a dose of 25 mg per kg.

Cell counts are done on days 0, 1, 2, 3, 4 and 7. The asterisks above the histograms indicate that the results obtained are significantly different from the levels observed before the treatment.

Figure 3A:
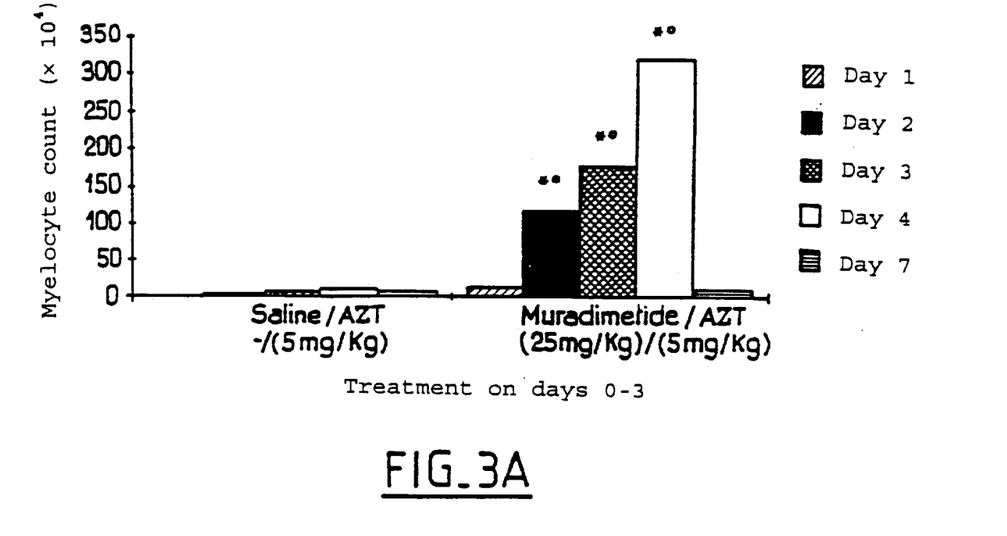
FIG. 3A relates to a nonmyelotoxic dose of AZT (5 mg/kg) and FIG. 3B to a myelotoxic dose (40 mg/kg).
Figure 3B:
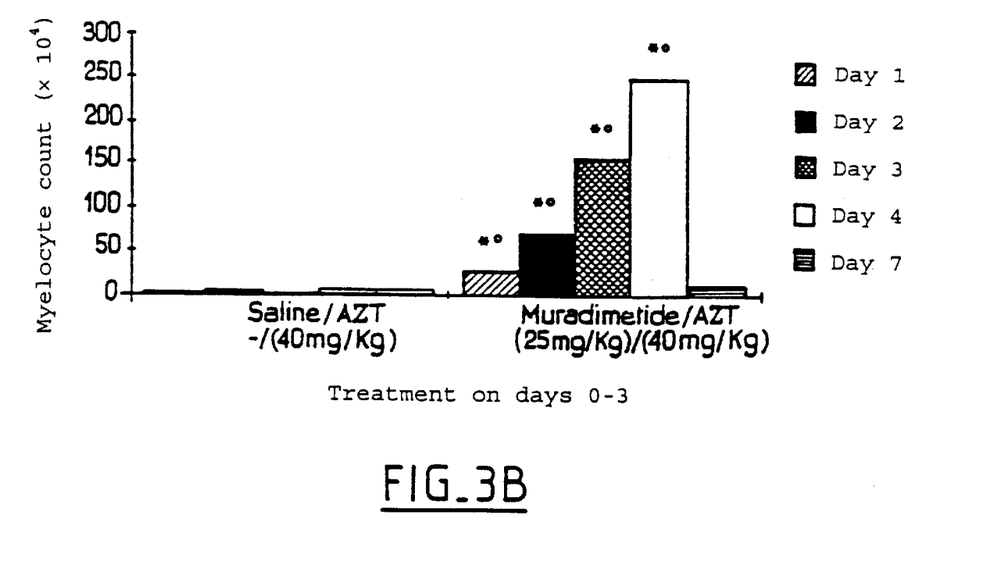
Figure 4:
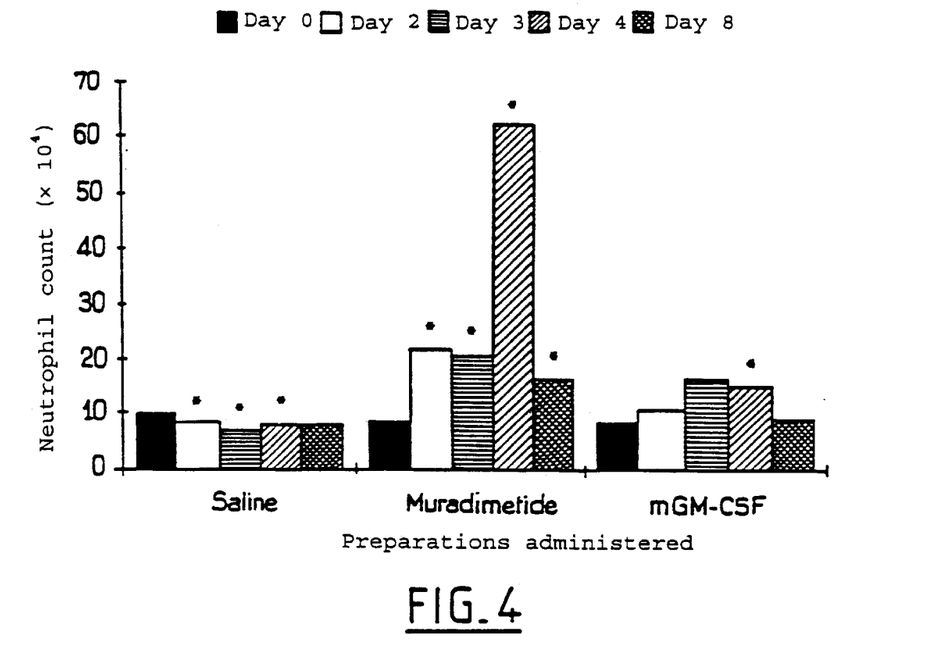
FIG. 4 represents the comparative effects of Muradimetide and of rmGM-CSF (recombinant mouse GM-CSF) on the circulating neutrophil count after administration of AZT.
Figure 5:
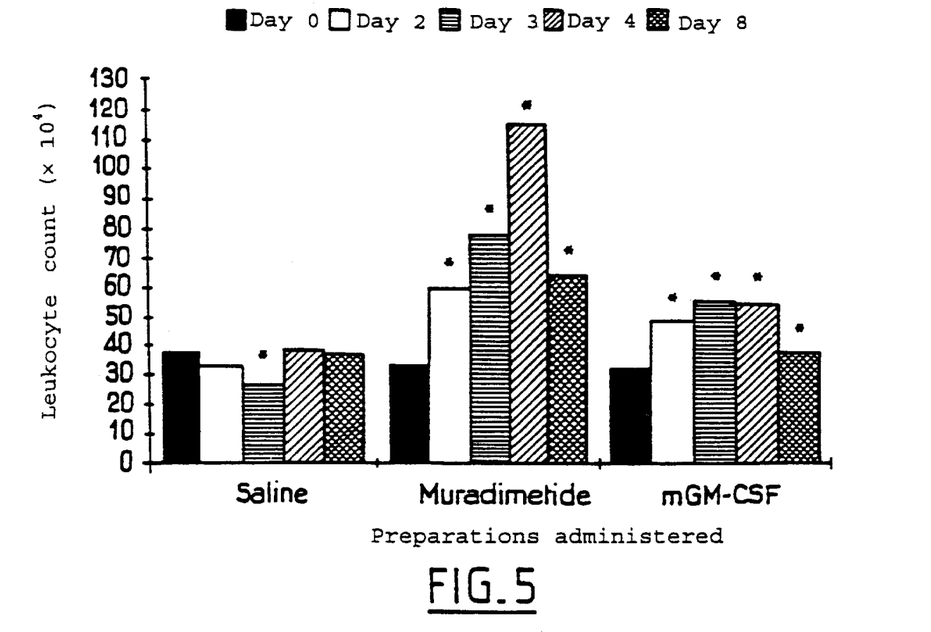
FIG. 5 represents the same comparison on the circulating leukocyte count.
Figure 6:
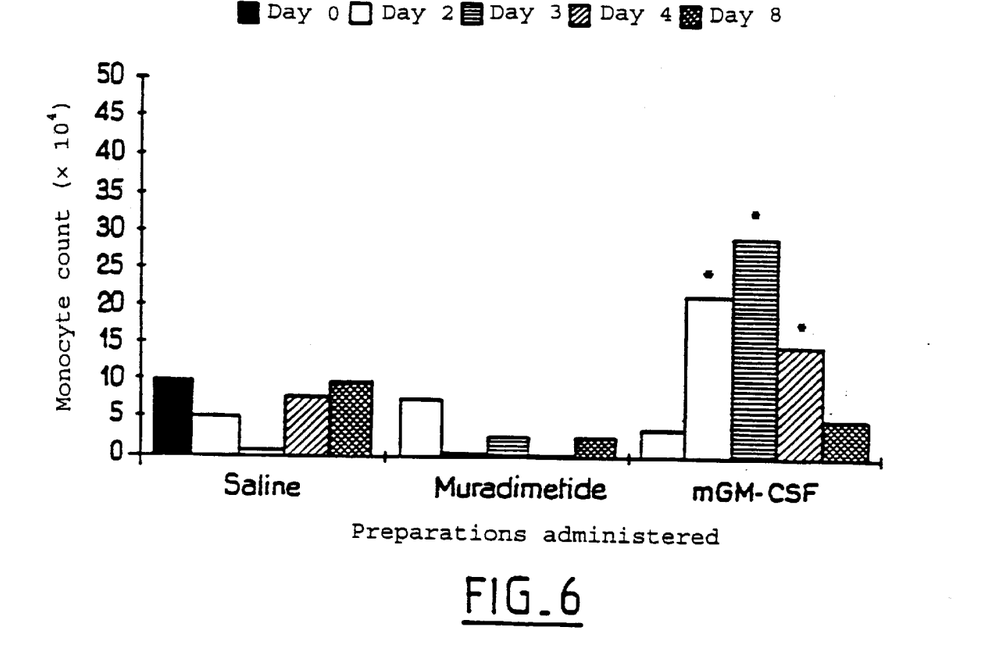
FIG. 6 represents the same comparison on the circulating monocyte count.

FIG. 3 represents the same experiment in which the myelocytes are counted.

In these three FIGS. 1, 2 and 3, it is clear that the effect is maximum 4 days after the beginning of the treatment. This is readily explained by the fact that the leukocytes and the neutrophils tend after this stimulation to regain their normal level and, as regards the myelocytes, the return to the baseline level means that this artificial stimulation is most advantageous for the cases mentioned above (gene therapy, marrow grafting, autografting, and the like). The disappearance of this effect is normal as a result of the fact that the HSC differentiate into mature cells and/or establish themselves in the organs.

EXAMPLE 9

Comparison of the effects of Muradimetide and GM-CSF.

When mice which have received a treatment with AZT are treated with GM-SCF under the same conditions as those used for Muradimetide, the leukocyte and neutrophil counts do not display an increase, contrary to what is observed when the AZT-Muradimetide combination is used. On the other hand, an increase in the number of monocytes is observed. FIGS. 4, 5, 6 and 7 show the effect of a treatment of mice with Muradimetide or with mGM-CSF on the changes in the circulating neutrophils, in the circulating leukocytes or in the circulating monocytes or in the circulating myelocytes, respectively, after an intravenous administration of AZT.

Female Swiss mice were treated intravenously with 40 mg per kg of AZT on days 0, 1, 2 and 3. The groups of mice (5 per group) receive, 4 hours before AZT, either physiological saline, or Muradimetide at 25 mg per kg or mGM-CSF at 125 µg per kg intravenously. Counts are done on days 0, 2, 3, 4 and 8. The asterisks above the histograms indicate that there is a significant difference in the count compared to the values obtained before the treatment on day 0. Hence it is seen that, while mGM-CSF is capable of giving rise to an increase in the number of monocytes, Muradimetide has a markedly pronounced effect on the neutrophils and the leukocytes. Furthermore, Muradimetide, unlike GM-CSF, induces a very strong elevation of the HSC in the blood.

Figure 7:
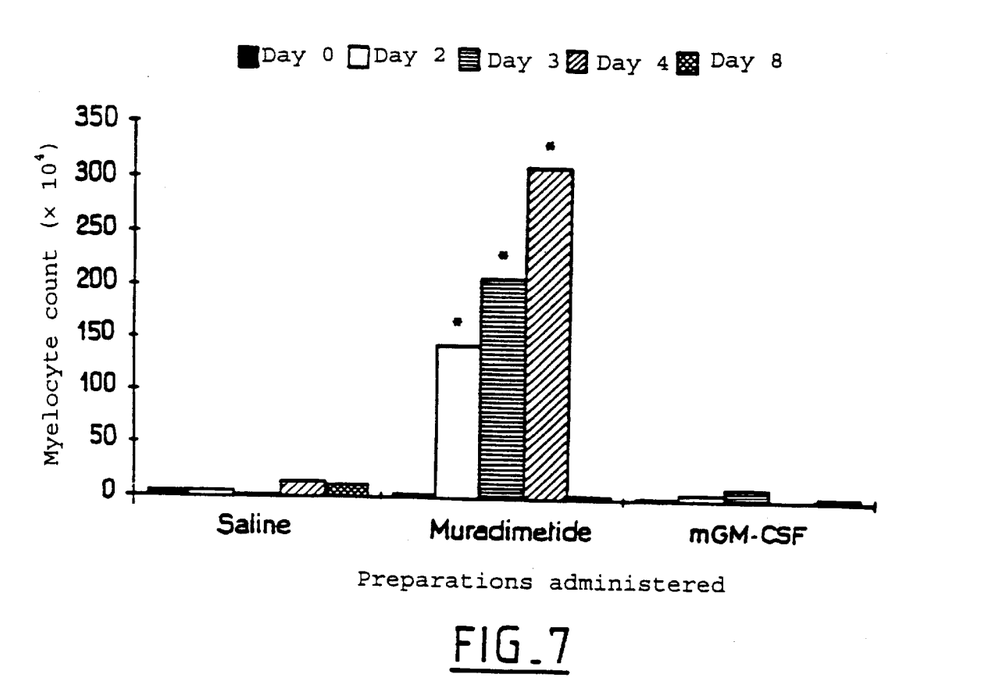
FIG. 7 represents the same comparison on the circulating myelocyte count.

The effect of Muradimetide compared to that of mGM-CSF is explicit in FIG. 7, which shows clearly that Muradimetide mobilizes HSC under conditions in which GM-CSF does not do so.

EXAMPLE 10

Comparison of the effect of Muradimetide with another MDP derivative.

Figure 8:
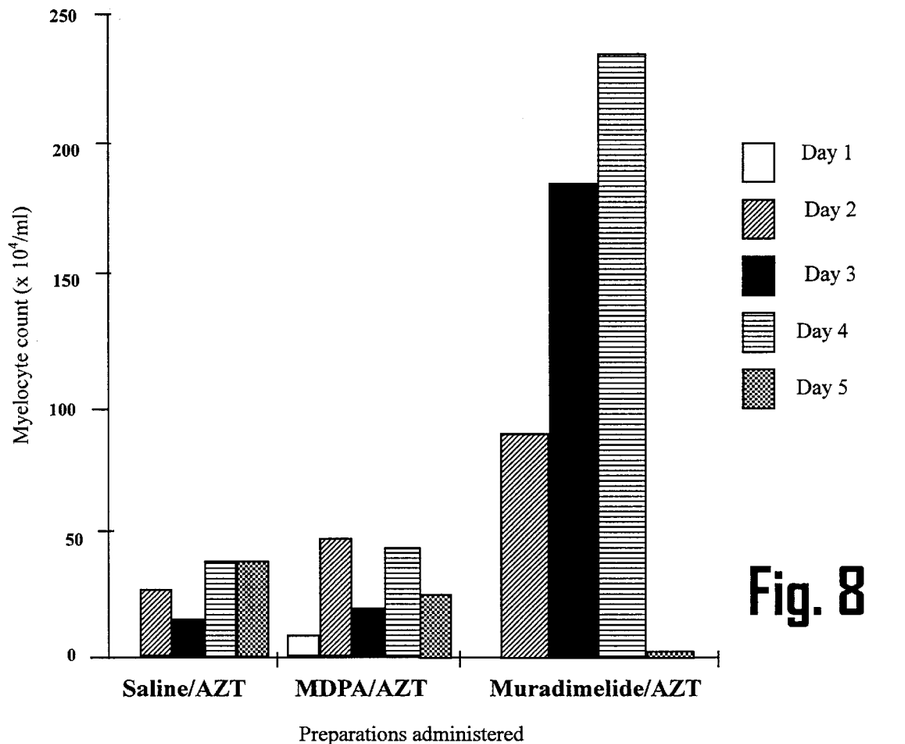
FIG. 8 represents the effect of an oral treatment with mice with Muradimetide on the change in the myelocyte count in the circulating blood, induced following an intravenous administration of AZT, two MDP derivatives being compared: MDPA (Nac—Mur—L—Ala—D—Glu) and Muradimetide.

The derivative used to demonstrate the special effect of Muradimetide is MDPA. FIG. 8 shows the effect on mice of an oral treatment on the changes in the myelocyte count induced following an intravenous administration of AZT. In this experiment, female Swiss mice were treated intravenously with 40 mg per kg of AZT on days 0, 1, 2 and 3. Groups of 5 mice received on the same four days, and 4 hours before AZT, either physiological saline, or MDPA at a dose of 25 mg per kg or Muradimetide orally at a dose of 25 mg per kg. Myelocyte counts were carried out on days 0, 2, 3, 4 and 8. The asterisks above the histograms have the same meaning as in the previous diagrams.

It is clearly apparent that the property of the derivatives of formula (I), and especially of Muradimetide, is not a property common to all muramyl peptides. This is especially well demonstrated by comparison with MDPA, of which Muradimetide is the diester derivative.

EXAMPLE 11

Synthesis of N-acetylmuramyl-L-alanyl-D-glutaminic α-methyl ester γ-L-alanine 3'-azido-3'-deoxythymidine (formula V).

This synthesis comprises the following steps:

a) Synthesis of Boc-L-alanine 3'-azido-3'-deoxythymidine (1).

206 mg (1 mmol) of N,N'-dicyclohexylcarbodiimide are added to 189 mg (1 mmol) of Boc-L-alanine dissolved in 20 ml of anhydrous dimethylformamide containing 102 mg (1 mmol) of dimethylaminopyridine. 267 mg (1 mmol) of 3'-azido-3'-deoxythymidine (AZT) are added to the reaction mixture, which is stirred for 24 hours at room temperature. After filtering off the precipitate of dicyclohexylurea, the reaction mixture is concentrated under vacuum. The product is finally obtained after purification on a column of silica gel.

b) Synthesis of L-alanine 3'-azido-3'-deoxythymidine hydrochloride (2):

260 mg (0.6 mmmol) of (1) are dissolved in 2 ml of a 1 N solution of hydrochloric acid in glacial acetic acid. After 30 minutes at room temperature, the reaction mixture is concentrated to dryness. The residue obtained is taken up in acetone and concentrated to dryness. The process is repeated several times and the residue, dried under vacuum, is used directly in the next step: 225 mg (100%).

c) Synthesis of N-acetylmuramyl-L-alanyl-D-glutamic α-methyl ester γ-L-alanine 3'-azido-3'-deoxthymidine (3) (formula V):

0.11 ml (1 mmol) of N-methylmorpholine and 0.13 ml (1 mmol) of isobutyl chlorocarbonate are added successively at −15° C. to 507 mg (1 mol) of N-acetylmuramyl-L-alanyl-D-glutamic α-methyl ester ( ) dissolved in 10 ml of anhydrous dimethylformamide. After 5 minutes, 225 mg (0.60 mmol) of (2) dissolved in 5 ml of dimethylformamide, cooled to −15° C., containing 0.11 ml of N-methylmorpholine, are added. The reaction mixture is stirred for 24 hours at −15° C. and then concentrated under vacuum. The product is finally obtained after purification on a column of Lichroprep RP18 (Merck) by elution in a mixture of ethanol and water. (3) is finally obtained by lyophilization of its aqueous solution: 272 mg (60%).

EXAMPLE 12

Synthesis of 6-0-(succinyl-3'-azido-3'-deoxythymidine)-N-acetylmuramyl-L-alanyl-D-glutamic dimethyl ester (formula VI).

a) Synthesis of α-benzyl-N-acetylmuramyl-L-alanyl-D-glutamic dimethyl ester (1):

1.4 g (2 mmol) of α-benzyl-4,6-OBzi-N-acetylmuramyl-L-alanyl-D-glutamic dimethyl ester (1) are treated under reflux in the presence of 100 ml of 56% aqueous acetic acid until dissolution is complete. The reaction mixture is concentrated under vacuum. The residue obtained is taken up and concentrated successively in water, toluene and methanol, and then dried under vacuum. (1) is purified on a column of silica gel by elution with a mixture of chloroform and methanol: 305 mg (50%).

b) Synthesis of 6-0-succinyl-N-acetylmuramyl-L-alanyl-D-glutamic dimethyl ester (2):

To 300 mg (1 mmol) of (1) dissolved in 10 ml of anhydrous pyridine are added to 44 mg (4 mmol) of succinic anhydride. The reaction mixture is stirred at room temperature for 4 days and then concentrated under vacuum. The residue obtained is taken up in acetone and concentrated several times, then dried under vacuum. The product obtained (α-benzyl-6-0-succinyl-N-acetylmuramyl-L-alanyl-D-glutamic dimethyl ester) is dissolved in 15 ml of glacial acetic acid and hydrogenated over 4 hours at atmospheric pressure in the presence of 100 mg of 5% Pd on charcoal. After filtering off the catalyst, the reaction mixture is concentrated under vacuum. The residue obtained is taken up in acetone and concentrated several times, then dried under vacuum. It is then taken up in water and purified on a column of AG1X2(H+)(BIORAD) by elution with an aqueous acetic acid gradient. (2) is finally obtained by lyophilization of its aqueous solution: 450 mg (70%).

c) Synthesis of 6-0-(succinyl-3'-azido-3'-deoxy-thymidine)-N-acetylmuramyl-L-alanyl-D-glutamic dimethyl ester (3) (formula VI):

0.05 ml (0.5 mmol) of N-methylmorpholine and 0.06 ml (0.5 mmol) of isobutyl chlorocarbonate are added successively at −15° C. to 320 mg (0.5 mmol) of (2) dissolved in 10 ml of anhydrous dimethylformamide. After 5 minutes, 267 mg (1 mmol) of 3'-azido-3'-deoxythymidine (AZT) are added. The reaction mixture is stirred for 24 hours at 15° C. and then concentrated under vacuum. The product is finally obtained after purification on a column of Lichroprep RP1i (Merck) by elution in a mixture of ethanol and water. (3) is finally obtained by lyophilization of its aqueous solution: 440 mg (50%).

The compounds of formulae (I), (II) and (III) on the one hand, in combination or otherwise with a derivative of formula (IV), or new conjugates corresponding to the formulae (V) and (VI) which are, in fact, covalent bondings of the compounds of formula (I) with compounds of formula (IV), afford a new class of medicaments displaying a very broad spectrum of use; apart from the examples mentioned and claimed, they should be able to be used whenever reestablishment of the differential cell count in the blood is necessary or when, for any reason, access to myelocytes via the blood circulation is necessary. The HSC are totipotent cells of extreme importance, as is explained at the beginning of this description. By means of this invention, access to them by taking a single blood sample, either as biological tools or for therapeutic purposes, becomes possible without lengthy and painful manipulations.

What is claimed is:

1. A method for inducing undifferentiated hematopoietic stem cell stimulation and their mobilization into the circulating blood, said method comprising the step of:
administering to a mammal in need of such treatment a pharmaceutical composition comprising as an active principal muradimetide of the formula:
Nac—Mur—L—Ala—D—Glu—[OCH$_3$]—OCH$_3$ in a pharmaceutically acceptable vehicle.

2. The method according to claim 1, wherein said muradimetide is administered at a dose between 0.1 to 25 mg per kg body weight.

3. The method according to claim 1, further comprising the step of administering a nucleoside derivative of the general formula:

(IV)

wherein B is a purine or a pyrimidine base and R is H, N$_3$ or a halogen.

4. The method according to claim 3, wherein said nucleoside derivative is 3'azido-3'doexythymidine.

5. The method according to claim 3, wherein said nucleoside derivative is administered at a dose between 1 and 150 mg/kg.

6. The method according to claim 3, wherein said muradimetide is administered orally.

7. The method according to claim 3, wherein said muradimetide is administered systemically.

8. The method according to claim 3, wherein said nucleoside derivative is administered orally.

9. The method according to claim 3, wherein said nucleoside derivative is administered systemically.

10. A method for inducing hematopoietic stem cell stimulation and mobilization into the circulating blood, said method comprising the step of:
administering to a mammal in need of such treatment a pharmaceutical composition comprising as an active principal muradimetide of the formula:
Nac—Mur—L—Ala—D—Glu—OCH$_3$ and a nucleoside derivative of the general formula:

(IV)

wherein B is a purine or pyrimidine base and R is H, N$_3$ or a halogen in a pharmaceutically acceptable vehicle.

11. The method according to claim 10, wherein said nucleoside derivative is 3'-azido-3'-deoxythymidine.

12. The method according to claim 10, wherein said muradimetide is administered at a dose between 0.1 to 25 mg per kg body weight.

13. The method according to claim 10, wherein said nucleoside derivative is administered at a dose between 1 and 150 mg/kg.

* * * * *